United States Patent [19]

de Haan et al.

[11] Patent Number: 5,441,747
[45] Date of Patent: Aug. 15, 1995

[54] STABILIZED SOLID PHARMACEUTICAL COMPOSITION CONTAINING ACID ADDITION SALTS OF A BASIC DRUG AND AN ALKALINE STABILIZER

[75] Inventors: Pieter de Haan, Oss; Cornelus J. M. van der Ven, Uden, both of Netherlands

[73] Assignee: Akzo N.V., Arnhem, Netherlands

[21] Appl. No.: 194,182

[22] Filed: Feb. 9, 1994

Related U.S. Application Data

[63] Continuation of Ser. No. 938,325, Aug. 31, 1992, Pat. No. 5,292,520, which is a continuation of Ser. No. 842,278, Feb. 19, 1992, abandoned, which is a continuation-in-part of Ser. No. 581,859, Sep. 13, 1990, abandoned.

[51] Int. Cl.$^6$ .................................. A61K 9/20
[52] U.S. Cl. ................................ 424/465; 424/499
[58] Field of Search ........................ 424/465, 499

[56] References Cited

U.S. PATENT DOCUMENTS

| | | | |
|---|---|---|---|
| 2,018,410 | 10/1935 | McDonald et al. | 167/93 |
| 2,287,699 | 6/1942 | Moss et al. | 23/109 |
| 3,012,852 | 12/1961 | Nelson | 23/109 |
| 3,411,873 | 11/1968 | Harnisch et al. | 23/109 |
| 4,743,450 | 5/1990 | Harris et al. | 424/440 |
| 4,834,985 | 5/1989 | Elger et al. | 424/484 |
| 5,066,495 | 11/1991 | Moro et al. | 424/451 |
| 5,096,714 | 3/1992 | Kuhrts | 424/439 |
| 5,102,666 | 4/1992 | Acharya | 424/487 |

FOREIGN PATENT DOCUMENTS

| | | |
|---|---|---|
| 0380021 | 8/1990 | European Pat. Off. |
| 2741513 | 3/1979 | Germany |
| 1548465 | 7/1979 | United Kingdom |

*Primary Examiner*—Thurman K. Page
*Assistant Examiner*—Neil Levy
*Attorney, Agent, or Firm*—Mary E. Gormley

[57] ABSTRACT

Disclosed are stabilized dry chemical (e.g. pharmaceutical) compositions containing the water soluble acid addition salt of a poorly soluble basic compound (e.g. mianserin, apomorphine, chlorpromazine, imipramine, or promethazine); an excipient selected from the group consisting of microcrystalline cellulose, lactose, calcium hydrogen phosphate, and mixtures thereof; and a water soluble (>2 mg/ml) alkaline stabilizer. The resulting dry composition are relatively more bioavailable and stable than compositions not containing the water soluble alkaline stabilizer, especially after high temperature (>45°) granulation processes. The process for preparing the dry composition is also more "rugged" with the added water soluble alkaline stabilizer.

4 Claims, No Drawings

STABILIZED SOLID PHARMACEUTICAL COMPOSITION CONTAINING ACID ADDITION SALTS OF A BASIC DRUG AND AN ALKALINE STABILIZER

This is a continuation of application Ser. No. 07/938,325 filed Aug. 31, 1992, Pat. No. 5,292,520 which is a file wrapper continuation of U.S. Ser. No. 07/842,278 abandoned, filed Feb. 26, 1992, which is a continuation-in-part of U.S. Ser. No. 07/581,859, filed Sep. 13, 1990, now abandoned.

BACKGROUND OF THE INVENTION

1. Field

This invention relates to chemical compositions generally, especially to stable solid pharmaceutical preparations containing the water soluble acid addition salt of a poorly soluble basic compound.

2. State of the Art

Methods for making tablets and other solid or dry pharmaceutical preparations are well-known. For example in Chase, et al, *Remington's Pharmaceutical Sciences*, pp. 1553–1576 (16th ed. 1980, Mack Publ. Co. of Easton, Pa., U.S.A.), methods of making tablets, capsules and pills and their respective components are described.

Two methods of making tablets are the "wet-granulation" and "dry-granulation" methods. The dry granulation method is especially suitable for medicinal compounds which are sensitive to moisture or are unable to withstand elevated drying temperatures associated with the wet-granulation methods.

Even with the use of these granulation methods however, the tableting of certain compounds (e.g. the water soluble acid addition salts of poorly soluble basic drugs) is less than ideal. Granulation processes using these compounds are not very "rugged", i.e. the processes have relatively strict tolerances making the granulation process extremely sensitive to changes in process variables (e.g. temperature and moisture changes). A process which is not very rugged has relatively strict operating tolerances which make the process sensitive to changes in processing variables. This is especially disadvantageous with regard to high temperature granulation processes which involve high temperatures and high humidities.

Even after tablets or other dry dosage pharmaceutical preparations are made containing the water soluble acid addition salts of poorly soluble basic drugs, the resulting preparations are generally not very stable. They discolour and/or degrade under certain conditions. For example, they may discolour or degrade upon exposure to light, relatively high humidity, or elevated temperatures. Color changes and degradation are tokens of instability. These tokens of instability may occur rather rapidly, sometimes within months, forcing a pharmacist or wholesaler storing the tablets to restock the product frequently.

The compound sodium pyrophosphate ($Na_4P_2O_7$) has been described as stabilizing certain calcium phosphate compounds. For example in U.S. Pat. No. 2,287,699 to Moss et al, alkali metal pyrophosphates (e.g. $Na_4P_2O_7$) are used to prepare a stabilized form of dicalcium phosphate (e.g. $CaHPO_4.2H_2$). In U.S. Pat. No. 3,012,852 to Nelson et al, a process for producing "internally stabilized" dicalcium phosphate dihydrate using pyrophosphate ions is also disclosed.

Certain magnesium compounds are also known to stabilize calcium phosphate compounds. For example in U.S. Pat. No. 2,018,410 to McDonald et al, trimagnesium phosphate, magnesium sulfate, magnesium stearate, and dimagnesium phosphate are all described as stabilizing hydrated dicalcium phosphate compounds substantially free from monocalcium phosphate for use in dentifrice preparations. In GB 1,548,465 to Hoechst Aktiengesellschaft, dimagnesium phosphate trihydrate is used to stabilize dicalcium phosphate dihydrate. In U.S. Pat. No. 3,411,873 to Harnisch et al, a process for stabilizing dicalcium phosphate dihydrate by means of a magnesium phosphate is disclosed.

In German patent application DE 2,741,513 to J. H. Benckiser GmbH, a procedure is described for stabilizing calcium hydrogen phosphate dihydrate against hydrolysis using a diphosphonic acid or its water-soluble salt.

In European Patent 054,333 to Stauffer Chemical Co., fine particles of a calcium phosphate (e.g. calcium pyrophosphate) are compacted under pressure to form a sheet. The sheet may then be comminuted to give a granular material. This granular material may then be used as an excipient in pharmaceutical tablets or wafers.

U.S. Pat. No. 4,743,450 to Harris et al discloses pharmaceutical compositions containing a drug (i.e. an ACE inhibitor), an alkaline stabilizer, and a saccharide. Harris et al prefers water insoluble stabilizers such as magnesium carbonate, calcium carbonate, and magnesium silicate, which have not always proved adequate in trying to stabilize a high temperature, high humidity granulation process. Harris et al also specifically requires a saccharide component in the described compositions, which unnecessarily adds to the costs of such compositions. Harris et al furthermore does not disclose any methods of increasing the ruggedness of a granulation procedure, nor does the reference disclose rugged granulation procedures utilizing temperatures greater than 45° C. It is now found that when the drying temperature exceeds 45° C., such procedures become less rugged. The same criticality is found with regard to granulation temperatures.

European patent application 380,021 to Abbott Laboratories discloses that buffers may be used to obtain complete solubilization of certain drugs, and that these buffers can increase the thermal stability of a drug formulation during the drying step of the granulation process. It also discloses solid dosage forms having increased stability which may contain estropipate, a tromethamine buffer, and an additional alkaline buffering agent, such as dibasic sodium phosphate. The dosage forms may also contain an excipient, such as dibasic calcium phosphate.

To date no one has been able to economically increase the ruggedness of a high temperature mixing step of granulation procedures involving certain unstable chemical compounds (e.g. the water soluble acid addition salt of a poorly soluble basic compound).

SUMMARY OF THE INVENTION

Generally, the invention includes a dry chemical composition containing the water soluble acid addition salt of a poorly soluble basic compound (e.g. a drug); an excipient selected from the group consisting of microcrystalline cellulose, lactose, calcium hydrogen phosphate, and mixtures thereof; and a water soluble alkaline stabilizer. The dry composition is relatively more stable than a composition not containing the water soluble alkaline stabilizer. Including the water soluble alkaline stabilizer in the process for preparing the dry pharmaceutical preparation makes the process surprisingly more "rugged" with respect to stabilization of the drug, especially with regard to high temperature and high humidity granulation techniques.

poorly soluble basic compounds for use in the invention include mianserin, apomorphine, chlorpromazine, imipramine, and promethazine. The particular acid addition salts of the chosen compounds will be at least partially capable of stabilization, in the selected excipient, by the particular stabilizer during storage and during a high temperature (>45° C.) granulation process.

The preparation contains a sufficient amount of stabilizer (generally from 0.5 to 10% by weight of the dry pharmaceutical preparation) to stabilize the acid addition salt of the compound in the preparation for a desired time at a desired temperature. A typical stabilizer is soluble in water (>2 milligrams/milliliter (mg/ml)); is alkaline in aqueous solution; and should be acceptable (e.g. pharmaceutically) for the intended use of the preparation.

The invention also includes a method of increasing the ruggedness of a granulation procedure utilizing temperatures greater than 45° C., involving a mixture of water soluble acid addition salts of poorly soluble basic compounds, and an excipient selected from the group consisting of microcrystalline cellulose, lactose, calcium hydrogen phosphate and mixtures thereof including: adding an acceptable alkaline compound having a water solubility of at least 2 milligrams/milliliter to the mixture, the acceptable alkaline compound being present in an amount from about 0.5 to about 10 percent by the dry weight of the granulation mixture.

Besides increasing the ruggedness of the granulation procedure, the resulting compositions are surprisingly stable, having a longer shelf-life. Furthermore, the compounds contained within the resulting compositions do not migrate to the exterior of the composition as is sometimes the case with the prior art compositions, and fissures do not form in the compositions. Unexpectedly, pharmaceutical preparations made using the invention also have better bioavailability.

DESCRIPTION OF THE PREFERRED EMBODIMENTS

The stable dry composition is preferably a tablet, pill, capsule or powder. Tablets are the presently most preferred preparation, especially for pharmaceutical preparations.

The amount of drug in a dry pharmaceutical preparation will of course depend on the potency of the chosen drug and its intended use. The amount of drug used in a dosage unit is well-known to those skilled in the art, and depends on the particular acid addition salt used as the compound. Illustratively, tablets of mianserin hydrochloride contain from 10–60 mg of the acid addition salt; tablets (hypodermic) of apomorphine hydrochloride contain from 5 to 6 milligrams; tablets of chlorpromazine hydrochloride contain from 10 to 200 milligrams; tablets of imipramine hydrochloride contain from 10 to 50 milligrams; and tablets of promethazine hydrochloride contain from 12.5 to 50 milligrams of promethazine hydrochloride.

Methods of making the described poorly soluble basic (e.g. amine) drug for use in the preparation are known. For example, methods of making imipramine are disclosed in U.S. Pat. No. 2,554,736. Mianserin ("1,2,3,4,10,14b-hexahydro-2-methyl-dibenzo [c,f]pyrazino [1,2-a] azepine monohydrochloride), and similar compounds may be made according to the teachings of U.S. Pat. Nos. 3,534,041 and 4,128,641. Other poorly soluble basic drugs which can form water soluble acid addition salts are readily commercially available.

Acid addition salts are derived from pharmaceutically acceptable acids, such as hydrochloric acid, sulfuric acid, phosphoric acid, acetic acid propionic acid, glycolic acid, maleic acid, fumaric acid, malonic acid, succinic acid, tartaric acid, lactic acid, citric acid, ascorbic acid, benzoic acid, methanesulfonic acid and the like. Acid addition salts may be obtained by reacting the poorly soluble basic drug with an appropriate acid in a suitable solvent.

The excipient is selected from the group consisting of microcrystalline cellulose, lactose, calcium hydrogen phosphate, and mixtures thereof. The amount of the selected excipient generally varies from about 30 to about 80% by weight of the dry pharmaceutical preparation. Preferably the excipients will comprise 50 to 80% by weight of the dry pharmaceutical preparation.

Compounds useful to stabilize the tablets once made, and to make the hereinafter described granulation process more rugged, include sodium bicarbonate ($NaHCO_3$), ammonium carbonate, anhydrous sodium carbonate ($Na_2CO_3$), sodium carbonate monohydrate, sodium tartrate, sodium potassium tartrate, sodium citrate ($C_6H_5Na_3O_7.2H_2O$), sodium hydroxide (NaOH), calcium acetate, sodium acetate, dibasic sodium phosphate ($Na_2HPO_4.14H_2O$), anhydrous dibasic sodium phosphate, diammonium hydrogen phosphate (($NH_4)_2HPO_4$), calcium leavinulate ($C_{10}H_{14}CaO_6.2H_2O$), sodium pyrophosphate ($Na_4P_2O_7$), and mixtures thereof. Of these compounds sodium bicarbonate, ammonium carbonate, sodium citrate, dibasic sodium phosphate, anhydrous dibasic sodium biphosphate, diammonium hydrogen phosphate, sodium pyrophosphate and mixtures thereof are the most preferred.

The preparation preferably contains from 0.5 to 10% by weight of the dry pharmaceutical preparation of the stabilizer. Most preferably, the composition contains 1 to 5% by weight of the pharmaceutical preparation (e.g. 1 to 5% tablet weight).

As used herein, "stabilize" is a relative term. To stabilize means the ability to prevent or delay the onset of tokens of instability. For example, a composition would be deemed "stabilized" if, with the addition of a stabilizing compound ("stabilizer"), it took longer (e.g. 2 weeks instead of 1 week) to discolour in the presence of a destabilizing stimulus (e.g. storage of the solution at an elevated (60° centigrade (C.)) temperature).

Methods for making dry pharmaceutical formulations are well-known. Methods for making powders are described in *Remington's Pharmaceutical Sciences*, pp. 1534–1552, the contents of which are incorporated by this reference. Methods for making tablets, capsules and pills are disclosed in the same reference at pages 1553–1584, the contents of which are also incorporated by this reference.

The preparations are preferably made in a wet-granulation process as described in *Remington's Pharmaceutical Sciences* at pages 1560–1563. The formulations can be stabilized for high temperature drying by first dry mixing the stabilizer with the tablet excipients before adding a granulation liquid (e.g. EXAMPLE I). Alternatively, the stabilizer may also be dissolved in the granulation liquid. Combinations of these two methods may also be used.

Although eminently suited for use in pharmaceutical dosage units, the invention has broader general applications not necessarily involved with the medical field. The invention can be used wherever high temperature, high humidity granulation techniques are required for compositions containing water soluble acid addition salts of poorly soluble chemical compounds (e.g. fertilizers, antiseptic or disinfectant tablets, herbicides, etc.).

The invention is further explained by reference to the following illustrative examples:

EXAMPLE I

Preparation of stabilized tablets

In a 300 liter high shear mixer, four batches are prepared according to the following FORMULATION 1:

| FORMULATION | 1 (kg) | 2 (kg) |
| --- | --- | --- |
| mianserin.HCl | 10 | 10 |
| potato starch (intragranular) | 7.5 | 7.5 |
| methylcellulose | 1 | 1 |
| colloidal SiO$_2$ (intragranular) | 1 | 1 |
| NaHCO$_3$ | 2.5 | — |
| calcium hydrogenphosphate dihydrate | 74.2 | 76.8 |
| potato starch (intergranular) | 2.5 | 2.5 |
| colloidal SiO$_2$ (intergranular) | 1 | 1 |
| magnesium stearate | 0.2 | 0.2 |

The mianserin hydrochloride, colloidal silicon dioxide, calcium hydrogenphosphate dihydrate, dried potato starch and sodium bicarbonate are mixed for 3 minutes. The mixture is then granulated with an aqueous solution of methylcellulose (approximately 15 liters).

The four batches of granulates are dried according to procedures Ia, Ib, Ic and Id respectively.

Ia. A fluid bed dryer with granule bed temperature of about 45°–50° C. to a moisture level of approximately 3.2% and filled into closed containers.

Ib. A fluid bed dryer with granule bed temperatures of about 30°–35° C. to moisture levels of approximately 3.2% and filled into closed containers.

Ic. In a drying cabinet with granule bed temperatures of about 35°–40° C. to moisture levels of approximately 3.2% and filled into closed containers.

Id. In a drying cabinet with granule bed temperatures of about 45°–50° C. to moisture levels of approximately 3.2% and filled into closed containers.

The granules of Ia to Id are screened through a 3.5 and a 0.71 mm sieve respectively. The resulting batches are admixed with potato starch, colloidal silicon dioxide and finally with magnesium stearate, from which tablets of 100 mg are prepared on a rotary press.

EXAMPLE II

Preparation of tablets without added stabilizer.

With the same equipment and the same process as described in EXAMPLE I, four batches are also made of the preparation of FORMULATION 2 (i.e. the formulation sans stabilizing agent). The granulates are dried in a fluid bed drier and in the drying cabinet in the same conditions as described in Ia to Id of EXAMPLE I, and are referred to as IIa to IId respectively. After screening the granules, and admixing with potato starch, colloidal silicon dioxide and magnesium stearate, 100 mg tablets (total weight) are prepared.

EXAMPLE III

Ruggedness tests

The respective batches (i.e. batches Ia through Id and IIa through IId) are analyzed immediately after tableting. Batches IIa and IId almost immediately yellowed, while all other batches remain a bright white.

EXAMPLE IV

Accelerated destabilization tests

Various batches (i.e. batches Ia–Id and IIb and IIc) were analyzed by accelerated destabilization tests wherein the tablets were stored in closed containers and in unit dose strips at elevated temperatures for relatively short periods of time.

A. 40° C. from 0 to 14 days—All batches maintained their bright white appearance for the period of time tested.

B. 50° C. from 0 to 4 days—Batches Ia through Id maintained their bright white appearance for the period of time tested. Batches IIb and IIc began yellowing after 7 days in a closed container.

C. 60° C. from 0 to 4 days—Batches Ia through Id maintained their bright white appearance for the period of time tested. Batches IIb and IIc began yellowing after 4 days in a closed container. Batches IIb and IIc began yellowing after 7 days in a unit dose strip.

EXAMPLES V

Preparation of stabilized tablets

In a 300 liter high shear mixer, four batches are prepared according to the following FORMULATION 3:

| FORMULATION | | 3 (kg) | 4 (kg) |
| --- | --- | --- | --- |
| mianserin.HCl | | 10 | 10 |
| potato starch (intragranular) | | 7.5 | 7.5 |
| potato starch (intergranular) | | 2.5 | 2.5 |
| methylcellulose | | 1 | 1 |
| Na$_2$HPO$_4$ | | — | 3 |
| colloidal silicon dioxide | | 2 | 2 |
| magnesium stearate | | 0.6 | 0.6 |
| Dibasic calcium phosphate dihydrate | qsad | 100.0 | 100.0 |

In a high shear mixer (300 liters) Formulation 3 is prepared by mixing for four minutes the mianserin.HCl, half of the colloidal silicon dioxide, dibasic calcium phosphate dihydrate, and potato starch (6.5 kg (intragranular)). Then the granulation liquid, a mucilage of 1 kg of potato starch (intragranular) and 1 kg of methylcellulose in approximately 15 kg of heated water (90° C.) is added and granulation is commenced. Formulation 3 is dried in a fluid bed drier with a granule bed temperature of about 30° to 35° C. until a residual moisture content of about 3.2% is attained, and are then filled into closed (air-tight) containers. Exactly the same procedure for Formulation 4 is used with the exception that the 3 kg of Na$_2$HPO$_4$ is dry mixed with the other tablet constituents before addition of the granulation liquid.

The resulting batches are admixed with potato starch (2.5 kg), colloidal silicon dioxide, and finally with magnesium stearate. The respective batches are analyzed immediately after tableting. The batches prepared as FORMULATION 3 almost immediately yellow, while the batches prepared as FORMULATION 4 remain a bright white.

EXAMPLE VI

Ruggedness test combined with accelerated destabilization test (worst case scenario)

Three batches were prepared on a 2 kilogram scale in a 10 liter Gral high shear mixer with the following formulations respectively:

| FORMULATION | | 3 (kg) | 5&6 (kg) |
|---|---|---|---|
| mianserin.HCl | | 10 | 10 |
| potato starch (intragranular) | | 7.5 | 7.5 |
| potato starch (intergranular) | | 2.5 | 2.5 |
| methylcellulose | | 1 | 1 |
| $Na_4P_2O_7$ | | — | 3 |
| colloidal silicon dioxide | | 2 | 2 |
| magnesium stearate | | 0.6 | 0.6 |
| Dibasic calcium phosphate dihydrate | qsad | 100.0 | 100.0 |

Formulations 3, 5 and 6 were processed to granulates and tablets according to the with the hot mucilage of starch and methyl cellulose (90° C.) as described in EXAMPLE V, with the exception that the granules have dried in a vacuum cabinet at approximately 35° C. The differences are:

Formulation 3: no stabilizer

Formulation 5: with stabilizer dissolved in the hot mucilage before granulation.

Formulation 6: with stabilizer dry mixed with the drug and the excipients before granulation with the hot mucilage.

Results

Tablets of Formulation 3, 5, and 6 were stored at 60° C. for approximately 10 days. Tablets of Formulation 3 were discoloured, but the tables of Formulations 5 and 6 remain a bright white, irrespective of the severe stress during hot granulation and storage of the tablets in extreme conditions.

EXAMPLE VII

Bioavailability tests

The tablets resulting from Formulations 2, 5 and 6 were subject to a standard test for predicting bioavailability (Dissolution in 0.1N HCl with a USP paddle, 50 rpm). Formulations 5 and 6 dissolved faster than Formulation 2, showing a further advantage of the invention.

Reference herein to specific embodiments or examples should not be interpreted as limitations to the scope of the invention, which is defined by the appended claims.

What is claimed is:

1. A dry pharmaceutical preparation consisting essentially of a water soluble acid addition salt of a poorly soluble basic drug selected from the group consisting of apomorphine, chlorpromazine, imipramine, promethazine, and mianserin;

and excipients selected from the group consisting of microcrystalline cellulose, lactose, and calcium hydrogen phosphate in an amount from about 30 to about 80 percent by weight of the dry pharmaceutical preparation; and a water soluble alkaline stabilizer in an amount from about 0.5 to about 10 percent by weight of the dry pharmaceutical preparation, wherein said stabilizer is selected from the group consisting of sodium bicarbonate, ammonium carbonate, sodium citrate, dibasic sodium phosphate, anhydrous dibasic sodium biphosphate, diammonium hydrogen phosphate, sodium pyrophosphate and mixtures thereof.

2. The dry pharmaceutical preparation of claim 1 wherein said excipient is calcium hydrogen phosphate.

3. The dry pharmaceutical preparation of claim 2 wherein said poorly soluble basic compound is mianserin.

4. The dry pharmaceutical preparation of claim 3, wherein the water soluble alkaline stabilizer is from about 1 to about 5 percent by weight of the dry pharmaceutical preparation.

* * * * *